US 9,805,577 B2

(12) United States Patent
Haflinger et al.

(10) Patent No.: US 9,805,577 B2
(45) Date of Patent: Oct. 31, 2017

(54) MOTION SENSING NECKLACE SYSTEM (71) Applicant: Nortek Security & Control LLC, Carlsbad, CA (US)

(72) Inventors: James J. Haflinger, Carlsbad, CA (US); Jeffrey M. Sweeney, Carlsbad, CA (US)

(73) Assignee: Nortek Security & Control, LLC, Carlsbad, CA (US)

( * ) Notice: Subject to any disclaimer, the term of this patent is extended or adjusted under 35 U.S.C. 154(b) by 0 days.

(21) Appl. No.: 14/072,579

(22) Filed: Nov. 5, 2013

(65) Prior Publication Data
US 2015/0123785 A1 May 7, 2015

(51) Int. Cl.
G08B 21/04 (2006.01)
A61B 5/00 (2006.01)
A61B 5/11 (2006.01)

(52) U.S. Cl.
CPC ........ G08B 21/0446 (2013.01); A61B 5/1117 (2013.01); A61B 5/6822 (2013.01); A61B 5/6831 (2013.01)

(58) Field of Classification Search
CPC . A61B 5/1117; A61B 5/0006; A61B 5/02055; A61B 5/6822; G08B 21/0446; G08B 21/02; G08B 21/0423; G08B 21/0453; G08B 21/043; G06F 19/3487
USPC .................. 340/500, 531, 539.1, 539.11, 4.1
See application file for complete search history.

(56) References Cited

U.S. PATENT DOCUMENTS

| 5,742,233 | A | * | 4/1998 | Hoffman | G08B 21/023 340/10.41 |
|---|---|---|---|---|---|
| 8,217,795 | B2 | | 7/2012 | Carlton-Foss | 340/573.1 |
| 8,308,641 | B2 | | 11/2012 | Moroney, III et al. | 600/301 |
| 8,461,988 | B2 | | 6/2013 | Tran | 340/540 |
| 2006/0282021 | A1 | | 12/2006 | DeVaul et al. | 600/595 |
| 2007/0106167 | A1 | | 5/2007 | Kinast | |
| 2007/0252708 | A1 | | 11/2007 | Fujisawa et al. | 340/573.1 |

(Continued)

FOREIGN PATENT DOCUMENTS

| BE | EP 2087835 A1 * | 8/2009 | ........... A61B 5/0002 |
|---|---|---|---|
| EP | 2 087 835 A1 | 8/2009 | |

(Continued)

OTHER PUBLICATIONS

"International Application Serial No. PCT/US2014/064040, International Search Report dated Feb. 11, 2015", 3 pgs.

(Continued)

*Primary Examiner* — James Yang
(74) *Attorney, Agent, or Firm* — Schwegman Lundberg & Woessner, P.A.

(57) ABSTRACT

A motion sensing necklace comprising includes a pendant attached to lower ends of two lanyards. The pendant includes a help button for a user to generate a signal for help, and a battery to power the motion sensing necklace. A neck strap is attached to upper ends of the first and second lanyards. Two motion sensors are located within opposing ends of the neck strap. A microprocessor located within the neck strap processes signals from the motion sensors to determine whether motion has occurred. A transmitter or transceiver located within the neck strap transmits motion detection signals and alerts generated by the microprocessor.

17 Claims, 6 Drawing Sheets (56) References Cited

U.S. PATENT DOCUMENTS

| | | | |
|---|---|---|---|
| 2007/0296571 A1* | 12/2007 | Kolen | A61B 5/0002 340/539.11 |
| 2010/0217533 A1 | 8/2010 | Nadkarni et al. | 702/19 |
| 2010/0220841 A1* | 9/2010 | Holst | H04R 25/554 379/52 |
| 2010/0245078 A1 | 9/2010 | Nadkarni et al. | 340/539.11 |
| 2011/0066064 A1 | 3/2011 | Jangle et al. | 600/534 |
| 2011/0066383 A1 | 3/2011 | Jangle et al. | 702/19 |
| 2011/0288784 A1 | 11/2011 | Jangle et al. | 702/19 |
| 2012/0105223 A1 | 5/2012 | Weil | 340/539.11 |
| 2012/0146795 A1 | 6/2012 | Margon et al. | 340/573.1 |

FOREIGN PATENT DOCUMENTS

| | | | |
|---|---|---|---|
| EP | 2087835 A1 * | 8/2009 | |
| WO | WO-2015069707 A1 | 5/2015 | |

OTHER PUBLICATIONS

"International Application Serial No. PCT/US2014/064040, Written Opinion dated Feb. 11, 2015", 6 pgs.

* cited by examiner

MOTION SENSING NECKLACE SYSTEM

FIELD OF THE INVENTION

The present invention relates to a motion sensing necklace system.

BACKGROUND OF THE INVENTION

For many elderly individuals and other individuals with physical disadvantages, the propensity to fall and the risk of injury therefrom increases over time. According to U.S. health statistics, one out of three adults age 65 and older falls each year, and these fall events are a leading cause of injury and death for this age segment. Falls are the most common cause of injuries and hospital admissions for trauma such as lacerations, hip fractures and head trauma. Serious injury due to a fall may prevent a person from immediately contacting medical personnel or a caregiver, thereby exacerbating the injuries suffered.

Figure 6:
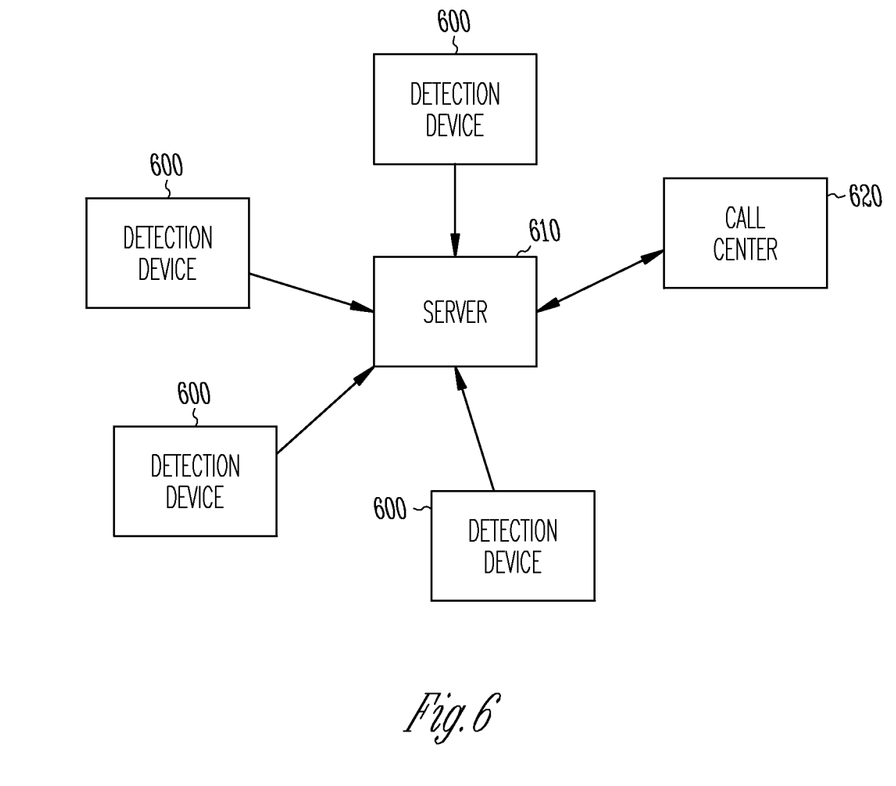
FIG. 6 is a block diagram of a conventional personal emergency reporting system.

In response to this problem, personal emergency reporting systems have evolved. Conventional personal emergency reporting systems sometimes take the form of an apparatus that a user keeps on their person and that includes a help button or switch that is pressed to alert others of a fall that requires help. The device may be worn on the wrist, attached to a belt, or carried in a pocket or purse, for example. However, depending on the severity of the injury, the user may not be able to reach and/or push the help button. For this reason, personal emergency reporting systems with embedded fall detection technology in their transmitters have evolved. An example of such a system is shown in FIG. 6. Detection apparatus 600 is worn by a user and has a fall detection sensor that incorporates an accelerometer and/or altimeter to record input data that is then processed using local firmware stored on apparatus 600 to determine the probability of a fall event. Upon determining based on the sensor data that a fall event has likely occurred, apparatus 600 automatically initiates and transmits an alarm event to a predetermined central monitoring station or server 610 and call center 620, typically via a personal emergency reporting system home console.

False positive fall detections are a significant problem with such systems. To help avoid false detections, the best location for the detection apparatus is on the user's torso, such as by being attached to a belt. However, users overwhelming prefer a detection apparatus that is configured as a necklace. In conventional necklace-type detection systems, the fall detection apparatus along with a battery is embedded within a pendant that is fastened to lanyard (necklace) and worn around the neck. As many fall detection devices incorporate an accelerometer, a challenge with having a fall detection device that is worn as a pendant around the neck is the high probability of a false positive fall detection due to excessive movement or swaying of the pendant during normal activities such as walking, moving from a standing position to a sitting position, or from a seated position to lying down. The pendant may also inadvertently hit an object such as a table or chair as the user changes positions from sitting to standing or from standing to sitting. Such an impact may generate a false positive fall detection in a device configured to detect shock as a fall event.

Thus, known necklace designs that use an accelerometer-based sensor in the pendant to measure acceleration, orientation and/or deviations from movement patterns increase the risk of generating false positive events due to the high propensity of excessive, non-regular and non-predictable movement or swaying of the pendant as a result of normal daily activities.

While accurately detecting and reporting fall events has substantial and tangible benefits, the ability to predict the likelihood of a fall event occurring based on movement patterns is arguably even more valuable. Fall prediction may be accomplished by identifying deviations in a person's gait from an established standard or "normal" gait of that particular individual. As with fall detection, a necklace design with an accelerometer embedded in the pendant makes fall prediction particularly difficult due to the propensity for excessive movement and swinging of the pendant. For this reason, in order to accurately measure and monitor an individual's gait for purposes of fall prediction, known devices must either be attached to or worn closely to the body.

The ability to remotely monitor movement and activity levels is also important in the elderly care industry from both wellness and security perspectives. However, for the same reasons as discussed above, a swinging pendant with an embedded accelerometer will less accurately measure the true activity level of an individual than will a device that is attached to or worn closely to the body.

Despite these disadvantages associated with known movement detection devices incorporating an accelerometer in a pendant of a necklace, as mentioned above, users overwhelmingly prefer this configuration to other configurations, such as a device attached to a belt. For this reason, there is a need for a necklace motion sensing system that provides a high degree of accuracy in motion sensing and detection of fall events, despite movement and swinging of the pendant.

SUMMARY OF THE INVENTION

The present invention provides a novel motion sensing necklace system that provides a higher degree of accuracy in fall detection and motion sensing relative to conventional necklace-based systems. The present invention also increased the wireless range of the device and provides greater battery housing space relative to conventional systems without substantially impacting the weight of the device.

A motion sensing necklace according to one embodiment of the invention comprises a pendant attached to lower ends of first and second lanyards. The pendant includes a help button for a user to generate a signal for help, and a battery to power the motion sensing necklace. A neck strap is attached to upper ends of the first and second lanyards, and at least two motion sensors are located within the neck strap. A microprocessor located within the neck strap processes signals from the motion sensors to determine whether motion has occurred, and a transmitter or transceiver located within the neck strap transmits motion detection signals and alerts generated by the microprocessor.

By providing a network of more than one sensor in more than one location in the necklace, accuracy is increased in the development of comprehensive movement profiles, including the ability to compare and contrast movement patterns, thresholds, orientation and/or other such profiles with different susceptibilities and influences to normal and abnormal body movements. The fixed positions of these multiple data points can be leveraged relative to the orientation or distance of each and/or relative to the normal worn position of the necklace. In addition, by locating the sensors in the upper neck strap region of the necklace, greater stability and more accurate motion detection is provided.

In one implementation, there are two motion sensors located at opposing ends of the neck strap, such that when the motion sensing necklace is worn by the user, the motion sensors are configured to be located on opposing and offsetting sides of a neck of the user or near an upper region of a collar bone of the user. By providing two sensor locations on opposing sides of the neck region or near the upper region of the collar bone, a superior design for motion sensing is provided. Use of two sensors configured in this fashion more accurately captures subtle shifts in the body during normal human movement, such as walking, as weight is transferred from one side of the body to the other.

In one implementation, the microprocessor and the transmitter are located within the neck strap between the microprocessor and the transmitter. By locating all primary electronics of the necklace within the neck strap, more available space for larger or additional batteries is provided within the pendant, while still maintaining an acceptable distribution of weight within the necklace. This creates multiple advantages including extending the operating life of the necklace, providing the ability to use components with higher power requirements such as a location transponder or gyroscope, and providing the ability for more frequent motion measurements and transmissions, such that the activity and motion of the user can be documented in greater detail. The perception of greater weight is not created by having a larger power source in the pendant, due to the distribution of the overall weight of the necklace between the upper neck region and the hanging pendant.

In one implementation, the neck strap comprises a casing that is hardened to protect the motion sensors, microprocessor and transmitter contained therein, and that is contoured to fit comfortably around the neck of the user.

In one implementation, conductive wiring extends through the first lanyard between the pendant and the neck strap, such that the help button and battery are conductively connected to the motion sensor, microprocessor and transmitter. At least one dedicated connectivity pathway is thereby provided between the pendant and the electronics within the neck strap.

In one implementation, an antenna is embedded within the second lanyard and extends from the neck strap towards the pendant. By embedding an antenna within one of the lanyards, a longer antenna may be deployed, with the result that the wireless range is approximately doubled in comparison to conventional antennas that are typically located within the pendant.

In one implementation, a breakaway safety clasp is provided between the second lanyard and the pendant. A safety feature to prevent the possibility of strangulation is thereby provided. By positioning the safety clasp near the pendant, greater user comfort is provided as compared to conventional designs where the clasp is located near the neck region. The connectors of the clasp may include a conductive material so as to form a continuous electrical circuit between all components of the motion sensing necklace, and an automatic alarm may be generated upon separation of the breakaway safety clasp.

In one implementation, the motion sensors are selected from a group consisting of accelerometers, gyroscopes, magnetometers and altimeters.

In one implementation, additional biometric sensors are embedded in the neck strap, such that parameters such as body temperature, pulse rate, oxygen saturation level and blood pressure may be measured. In addition, contacts may be provided in the neck strap or the pendant to determine whether the necklace is being worn by the user.

Another embodiment of the invention is a motion sensing necklace comprising a pendant attached to lower ends of first and second lanyards that includes a help button for a user to generate a signal for help, and a battery to power the motion sensing necklace. A neck strap is attached to upper ends of the first and second lanyards, and a motion sensor is located within the neck strap. A microprocessor located within the neck strap processes signals from the motion sensors to determine whether motion has occurred, and a transmitter located within the neck strap transmits motion detection signals and alerts generated by the microprocessor. Conductive wiring extends through one lanyard between the pendant and the neck strap, such that the help button and battery are conductively connected to the motion sensor, microprocessor and transmitter, and an antenna is embedded within the other lanyard and extends from the neck strap towards the pendant.

According to this embodiment, placement of a sensor in the upper region of the necklace to detect falls or motion provides a superior design due to greater stability as compared to sensors located in a free swinging pendant. This, in combination with a greater wireless range provided by a longer antenna embedded within a lanyard of the necklace, and the possibility of increasing the number and/or size of batteries in the pendant by locating the majority of the fall detection and other electronics in the neck region rather than in the pendant, provides a novel and advantageous motion detecting necklace.

Other features, elements, processes, steps, characteristics and advantages of the present invention will become more apparent from the following detailed description of the embodiments of the present invention with reference to the attached drawings.

DETAILED DESCRIPTION OF THE INVENTION

Figure 1:
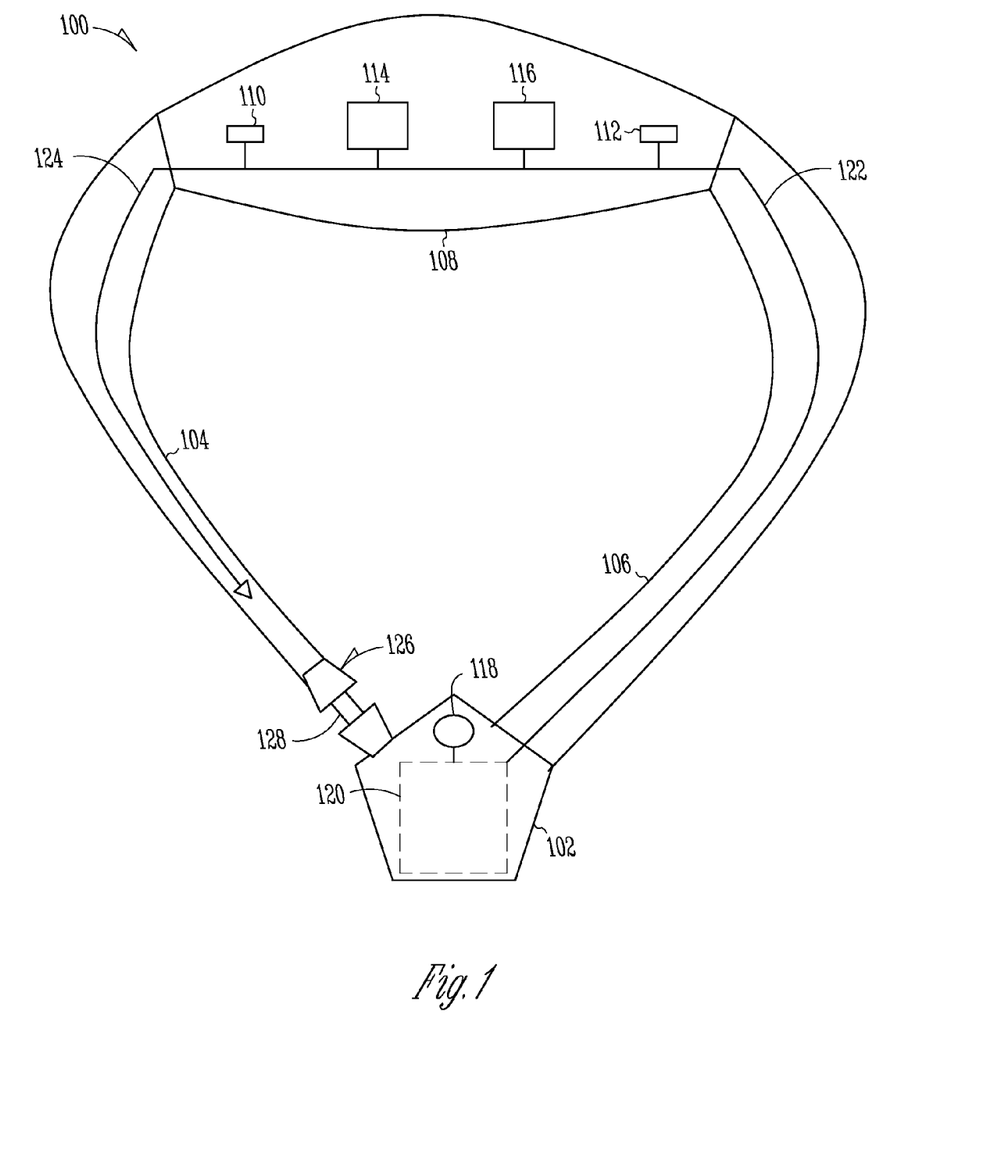
FIG. 1 illustrates a motion sensing necklace according to the present invention.

A motion detection necklace 100 according to the present invention is illustrated in FIG. 1. Necklace 100 comprises pendant 102 that is attached to lower ends of first and second lanyards 104, 106. A neck strap 108 is attached to the upper ends of lanyards 104, 106. When necklace 100 is worn, neck strap 108 rests against the user's neck while pendant 102 is suspended and hangs below the neck by lanyards 104, 106.

Neck strap 108 houses two or more sensors 110 and 112. Sensors 110 and 112 may be, for example, accelerometers, gyroscopes, magnetometers, altimeters or combinations of these or other components for detecting motion. As shown in FIG. 1, sensors 110 and 112 are positioned within opposing sides of neck strap 108, such that they are located on opposing and offsetting sides of the neck region or near the upper region of the collar bone. Microprocessor 114 is also located in neck strap 108 and processes signals from sensors 110 and 112 to determine whether a fall event and/or motion has occurred. RF transmitter 116, also located in neck strap 108, transmits fall detection alarms and other motion detection signals generated by microprocessor 114 via antenna 124 to the personal emergency reporting system home console, and then on to the central monitoring station (e.g. station 610 in FIG. 6). Alternatively, transmitter 116 may be a transceiver, for example, to provide the ability to update the firmware or algorithm on the necklace. That is, a receiver may be provided in addition to transmitter 116. In one embodiment, as sensors 110 and 112 are located at opposing ends of neck strap 108, processor 114 and transmitter 116 are located between sensors 110 and 112.

Neck strap 108 is in the form of a casing that is hardened to protect its internal electronics, and that is contoured so as to fit comfortably around the user's neck. In addition, neck strap 108 is configured to be sufficiently broad to house the system electronics, which also provides the advantage of increased stability for motion sensing.

Pendant 102 is attached to the lower ends of lanyards 104, 106 and includes help button or switch 118 and battery 120. Help button 118 and battery 120 are connected by conductive wiring 122 extending through one lanyard 106 to the circuitry within neck strap 108. Thus, there is at least one dedicated connectivity pathway between pendant 102 and the electronics within neck strap 108. Battery 120 powers sensors 110, 112, microprocessor 114 and transmitter 116 via wiring 122, and alarm signals generated by a press of help button 118 can be transmitted to microprocessor 114 and transmitter 116 via wiring 122.

By locating the primary electronics of necklace 100 (sensors 110, 112, processor 114, transmitter 116) within neck strap 108, more available space for larger or additional batteries is provided within pendant 102 as compared to conventional pendant design, while still maintaining an acceptable weight distribution in necklace 100. This creates multiple advantages including extending the operating life of necklace 100, providing the ability to use components with higher power requirements such as a gyroscope, and providing the ability for more frequent motion measurements and transmissions, such that the activity and motion of the user can be documented in greater detail. The perception of greater weight is not created by having a larger power source in the pendant, due to the distribution of the overall weight of the necklace between the upper neck region and the hanging pendant.

Long range antenna 124 is embedded within the other lanyard 104. Antenna 124 is connected to RF transmitter 116 to allow for transmission of status and alert signals to the personal emergency response system console, which are then conveyed on to the central monitoring station. Antenna 124 may have a monopole design extending from the electronics within neck strap 108 towards pendant 102, a loop design around neck strap 108, or a dipole design. By embedding antenna 124 within lanyard 104, a longer antenna may be deployed, with the result that the wireless range is approximately doubled in comparison to conventional antennas that are typically located within the pendant. Alternatively, or in addition, lanyard 104 may be used to provide an additional wiring pathway between pendant 102 and the electronics within neck strap 108.

Breakaway safety clasp 126 is provided between lanyard 104 and pendant 108 as a safety feature to prevent the possibility of strangulation. Safety clasp 126 is preferably located on the lanyard-side containing the antenna in order to avoid breaking the electrical connection between the electronics within pendant 102 and neck strap 108. By positioning safety clasp 126 near pendant 102, greater user comfort is provided as compared to conventional designs where clasp 126 is located near the neck region.

Connectors 128 of clasp 126 may include a conductive material such as copper such that, where a wiring pathway is provided within lanyard 104, a continuous electrical circuit is formed between all components of necklace 100. By creating a continuous electrical circuit within the necklace, an alarm may be automatically triggered in the event that the safety clasp becomes detached. A greater level of security for users is thereby provided during dramatic events, such as a fall, in which the necklace may become separated at the safety clasp due to the violent nature of the event, and perhaps thrown out of range of the user. Also, during such an event where the clasp is separated, the user may be unconscious, injured or otherwise unable to manually signal an emergency alert by pressing help button 118. By generating an automatic alarm whenever the continuous circuit is broken by separation of clasp 126, a greater level of redundancy is provided in the detection of a fall or a dramatic event, and the effectiveness of the invention as a safety device for the elderly is enhanced.

Necklace 100 may also include biometric sensors such as body temperature, pulse rate, oxygen saturation level, blood pressure and other types of sensors embedded in neck strap 108 in order to gather biometric data from the user, and/or contacts in neck strap 108 or a sensor in pendant 102 in order to determine whether necklace 100 is being worn. Alerts may be generated based on predetermined biometric data thresholds or measurements made by the biometric sensors.

By providing two sensor locations on opposing sides of the neck region or near the upper region of the collar bone, a superior design for motion sensing is provided as compared to a single sensor. Use of two sensors 110, 112 configured in this fashion more accurately captures subtle shifts in the body during normal human movement, such as walking, as weight is transferred from one side of the body to the other. A network of more than one sensor in more than one location on the necklace increases accuracy in the development of comprehensive movement profiles, including the ability to compare and contrast movement patterns, thresholds, orientation and/or other such profiles with different susceptibilities and influences to normal and abnormal body movements. The fixed positions of these multiple data points can be leveraged relative to the orientation or distance of each and/or relative to the normal worn position of the necklace (and as such, relative to the body of the user).

Although two sensors are preferred, in another embodiment, only a single sensor (e.g. accelerometer, gyroscope, magnetometer, altimeter or combinations thereof on a chip) is located in neck strap 108. The use of a single sensor in the upper region of necklace 100 is still superior for motion sensing and fall detection as compared to conventional designs that locate the sensor in the pendant. Use of an altimeter, for example, creates advantages by being placed higher on the body, thereby resulting in a greater height differential between both a standing and fallen position and a sitting and fallen position, and allowing fall events to be more accurately detected, as compared to conventional designs that locate the altimeter in the pendant.

Figure 2:
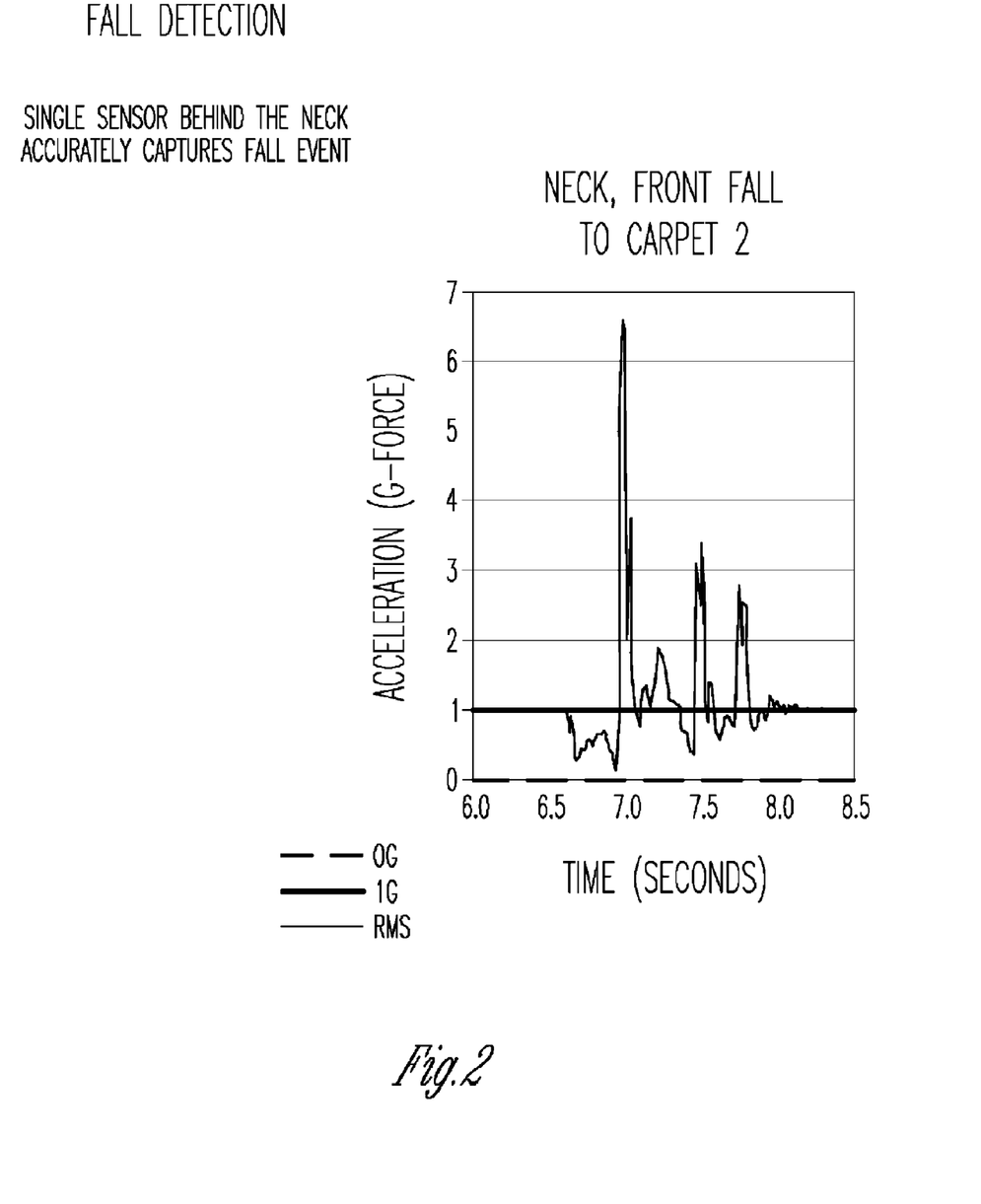
FIG. 2 is an acceleration profile of a fall event for a necklace employing a single sensor behind the neck according to the present invention.
Figure 3:
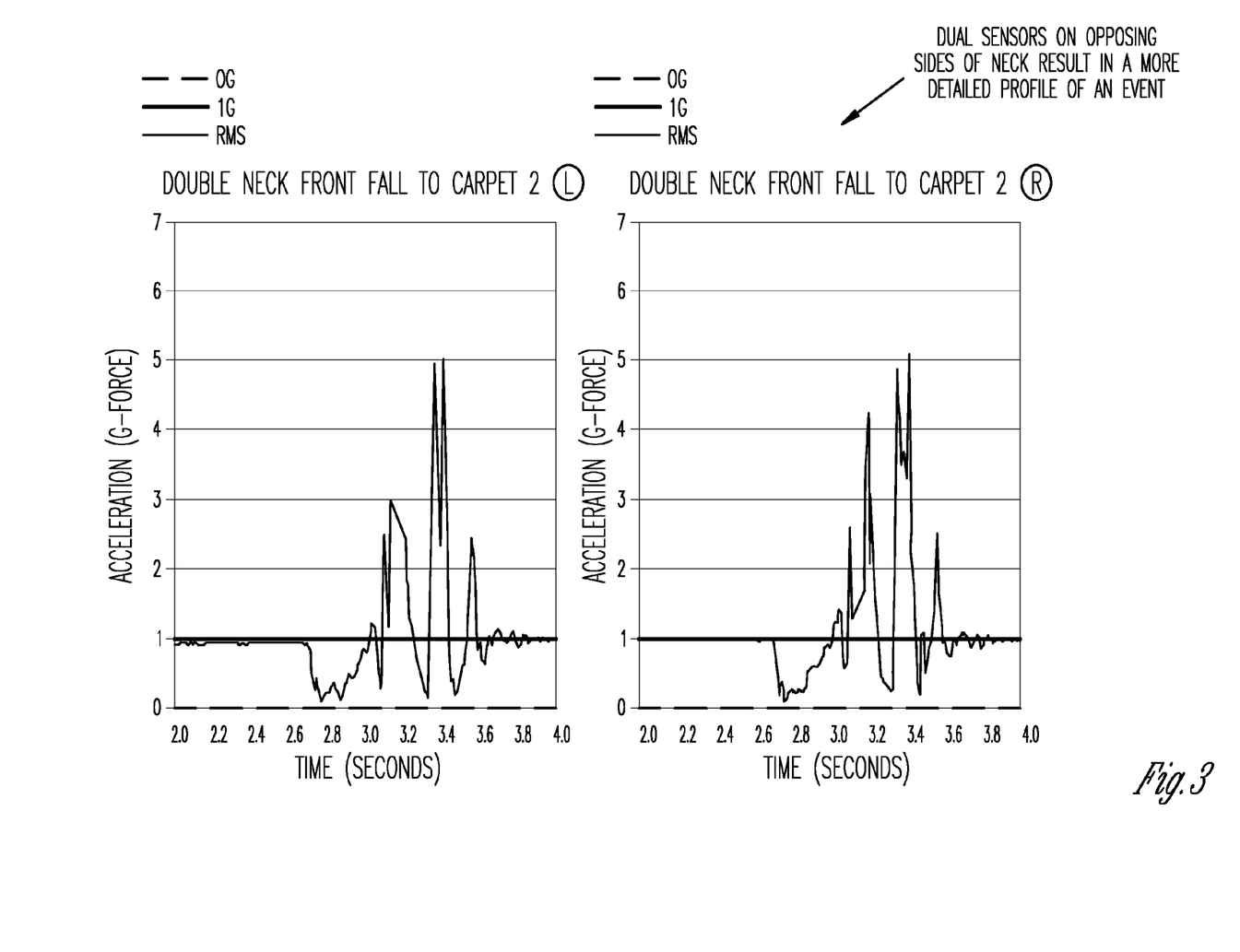
FIG. 3 is an acceleration profile of a fall event for a necklace employing dual sensors on opposing sides of the neck according to the present invention.
Figure 4:
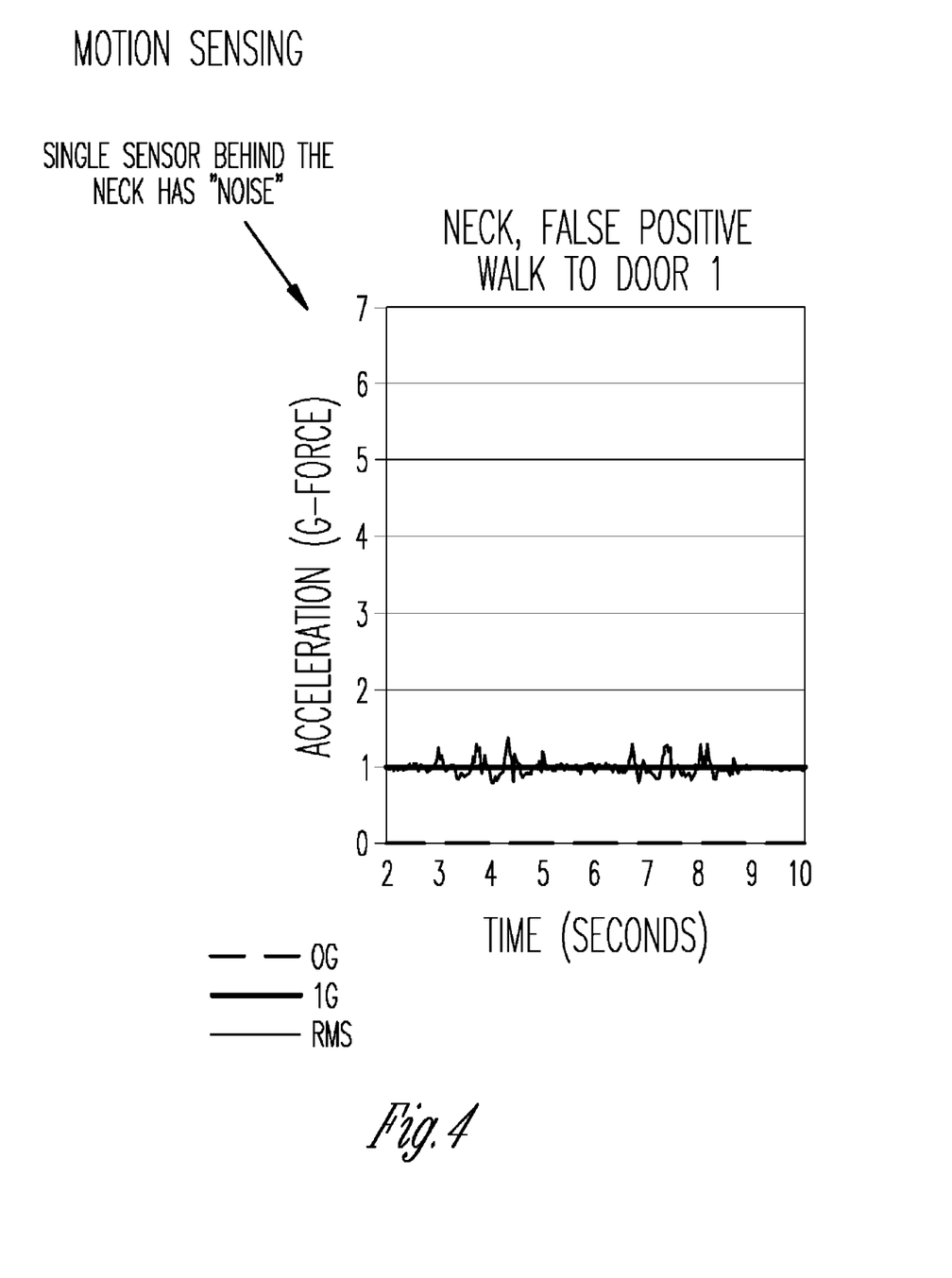
FIG. 4 is an acceleration profile of motion sensing for a necklace employing a single sensor behind the neck according to the present invention.
Figure 5:
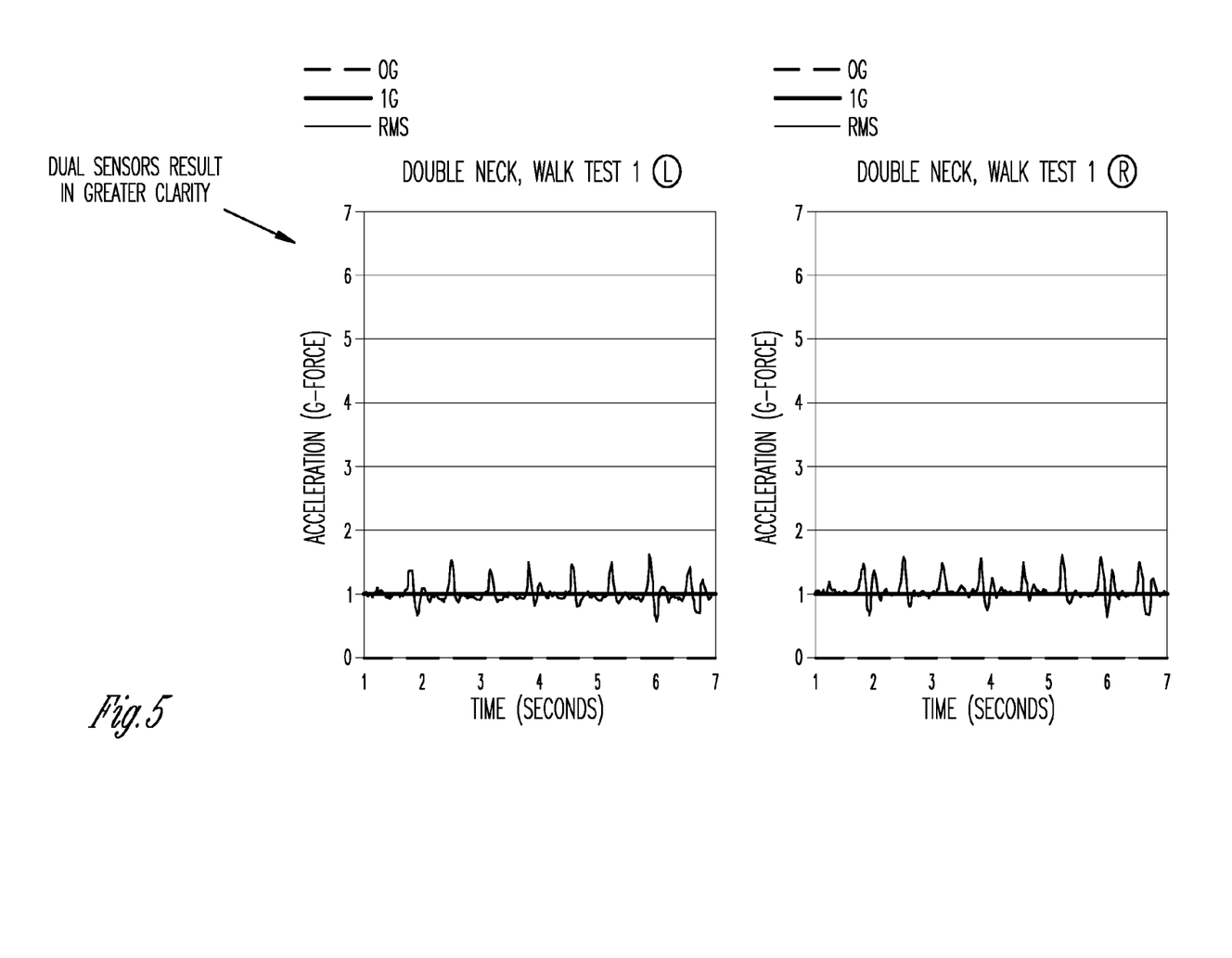
FIG. 5 is an acceleration profile of motion sensing for a necklace employing dual sensors on opposing sides of the neck according to the present invention.

The greater accuracy for both fall detection and motion sensing that is provided by use of two or more sensors on opposing sides of the neck, as opposed to a single sensor behind the neck, is illustrated in the acceleration profiles of FIGS. 2-5. FIG. 2 is an acceleration profile (acceleration vs. time) of a fall event for a single sensor behind the neck configuration, whereas FIG. 3 is an acceleration profile of a fall event for a dual sensors on opposing sides of the neck configuration. As can be seen in FIG. 2, a single sensor behind the neck accurately captures the fall event. However, as can be seen in FIG. 3, the use of dual sensors on opposing sides of the neck results in a more detailed profile of the event. FIG. 4 is an acceleration profile of motion sensing where a single sensor behind the neck is used, and FIG. 5 is an acceleration profile of motion sensing where dual sensors on opposing sides of the neck are used. As can be seen in FIG. 4, there is noise in the profile where the single sensor behind the neck is used. Where dual sensors are used, as in FIG. 5, there is less noise and greater clarity in the profile.

According to the present invention, placement of the sensor in the upper region of the necklace to detect falls or motion provides a superior design due to greater stability compared to sensors located in a free swinging pendant. The placement of two or more sensor locations on opposing sides of the neck region or near the upper region of the collar bones creates even greater advantages due to the ability to capture more granular and localized movement data in an individual as opposed to a single sensor.

Further, according to the present invention, a greater wireless range is provided by a longer antenna embedded within a lanyard of the necklace. Moreover, by locating the majority of the fall detection and other electronics in the neck region rather than in the pendant, the possibility of increasing the number and/or size of batteries in the pendant while still maintaining an acceptable weight range is provided.

While the invention has been described with respect to embodiments thereof, it will be apparent to those skilled in the art that the invention may be modified in numerous ways and may assume many embodiments other than those specifically set out and described above. For example, although the invention has been described in the context of a motion sensing necklace to be worn by elderly or physically disadvantaged individuals, the invention could also be implemented in a modified necklace attached to farm animals such as cattle and horses, or to other animals, in order to capture, track and analyze movement patterns. In another example, the invention could be implemented in a modified necklace for use in sports in order to capture, measure and analyze impacts, shocks and falls. In another example, the invention may be implemented as a necklace worn by drivers in order to detect by changes in posture drivers who are falling asleep. The appended claims cover these and all other modifications that fall within the true spirit and scope of this invention.

The invention claimed is:

1. A motion sensing necklace system comprising:
   at least two motion sensors coupled to a necklace, wherein when the necklace is worn by a user, the motion sensors are configured to be located on opposed and offset sides of a neck of the user, and the motion sensors are configured to sense respective different left and right side motion information about a particular motion of the user over a first duration and, in response, generate respective different time-varying left and right side motion profiles, wherein each of the motion profiles includes motion information corresponding to multiple different instances over the first duration, and wherein the particular motion of the user includes a weight shift from one side of the user's body to the other;
   a microprocessor configured to receive the respective different time-varying left and right side motion profiles, process the received motion profiles together to determine a comprehensive movement profile associated with the user wherein the comprehensive movement profile corresponds to the same particular motion of the user over the first duration that includes the weight shift from one side of the user's body to the other, and compare subsequent sensor information with the comprehensive movement profile to provide a comparison result, wherein the subsequent sensor information includes signals later received from the same motion sensors and includes motion information corresponding to multiple different instances over a different second duration; and
   a transmitter configured to transmit signals or alerts generated by the microprocessor and based on the comparison result.

2. The motion sensing necklace system of claim 1, further comprising a pendant attached to lower ends of first and second lanyards, the pendant including a help button and a battery; and
   a neck strap attached to upper ends of the first and second lanyards, wherein the at least two motion sensors are located at opposing ends of the neck strap.

3. The motion sensing necklace system of claim 2, wherein the microprocessor and the transmitter are located within the neck strap between the at least two motion sensors.

4. The motion sensing necklace system of claim 2, further comprising conductive wiring extending through the first lanyard between the pendant and the neck strap, such that the help button and battery are conductively connected to one or more of the motion sensor, microprocessor and transmitter.

5. The motion sensing necklace system of claim 4, further comprising a breakaway safety clasp between the second lanyard and the pendant, wherein the breakaway safety clasp triggers an alarm when the clasp is disconnected.

6. The motion sensing necklace system of claim 1, wherein the motion sensors are selected from a group consisting of accelerometers, gyroscopes, magnetometers and altimeters.

7. The motion sensing necklace system of claim 1, further comprising biometric sensors that are coupled to the necklace.

8. The motion sensing necklace system of claim 7, wherein the biometric sensors measure one or more of body temperature, pulse rate, oxygen saturation level and blood pressure.

9. The motion sensing necklace system of claim 8, wherein the microprocessor is configured to generate an alert based on predetermined biometric data thresholds or measurements made by the biometric sensors.

10. The motion sensing necklace system of claim 1, and further comprising contacts in the neck strap or the pendant to determine whether the necklace is being worn by the user.

11. A motion sensing necklace comprising:
    a pendant attached to lower ends of first and second lanyards; the pendant including a battery to power the motion sensing necklace;

a neck strap attached to upper ends of the first and second lanyards;

at least two motion sensors located within the neck strap at opposed and offset sides of a neck when the necklace is worn, the motion sensors configured to sense respective different left and right side motion information about a particular motion of a user over a first duration and, in response, generate respective different time-varying left and right side motion profiles, wherein each of the motion profiles includes motion information corresponding to multiple different instances over the first duration, and wherein the particular motion of the user includes a weight shift from one side of the user's body to the other;

a microprocessor located within the neck strap that processes the respective different time-varying left and right side motion profiles from the motion sensors to determine a user-specific comprehensive movement profile that corresponds to the same particular motion of the user over the first duration that includes the weight shift from one side of the user's body to the other, and to determine whether abnormal user motion has occurred by using a comparison of the user-specific comprehensive movement profile and subsequent sensor information to provide a comparison result, wherein the subsequent sensor information includes signals later received from the same motion sensors and each of the signals includes motion information corresponding to multiple different instances over a different second duration;

a transmitter located within the neck strap that transmits motion detection signals and alerts generated by the microprocessor;

conductive wiring extending through the first lanyard between the pendant and the neck strap, such that the help button and battery are conductively connected to the motion sensor, microprocessor and transmitter; and an antenna embedded within the second lanyard and extending from the neck strap towards the pendant.

12. The motion sensing necklace of claim 11, further comprising a breakaway safety clasp between the second lanyard and the pendant, wherein connectors of the breakaway safety clasp form a portion of a sensor that is configured to trigger an alarm when the connectors are disconnected.

13. The motion sensing necklace system of claim 4, further comprising an antenna embedded within the second lanyard and extending from the transmitter in the neck strap toward the pendant.

14. The motion sensing necklace system of claim 1, wherein the microprocessor is configured to identify a user fall event based on the comparison result.

15. The motion sensing necklace system of claim 1, wherein the microprocessor is configured to identify an abnormal user condition based on the comparison result.

16. The motion sensing necklace system of claim 1, wherein the microprocessor is configured to indicate a predicted fall event based on the comparison result.

17. The motion sensing necklace of claim 11, wherein the microprocessor is configured to generate a fall event prediction based on the user-specific movement profile and information received from both motion sensors.

* * * * *